(12) United States Patent
Alarcon Herrera et al.

(10) Patent No.: US 10,539,644 B1
(45) Date of Patent: Jan. 21, 2020

(54) TRACKING AN OBJECT IN AN ELECTROMAGNETIC FIELD

(71) Applicant: Northern Digital Inc., Waterloo (CA)

(72) Inventors: Jose Alarcon Herrera, Waterloo (CA); Andrew Wiles, Waterloo (CA); Asli Dinc, Waterloo (CA); Martin Kopcik, Waterloo (CA)

(73) Assignee: Northern Digital Inc., Ontario (CA)

( * ) Notice: Subject to any disclaimer, the term of this patent is extended or adjusted under 35 U.S.C. 154(b) by 0 days.

(21) Appl. No.: 16/287,383

(22) Filed: Feb. 27, 2019

(51) Int. Cl.
G01N 21/00 (2006.01)
G01S 1/70 (2006.01)
A61B 5/06 (2006.01)
A61B 34/20 (2016.01)

(52) U.S. Cl.
CPC .............. *G01S 1/70* (2013.01); *A61B 5/062* (2013.01); *A61B 34/20* (2016.02); *A61B 2034/2051* (2016.02); *A61B 2034/2055* (2016.02)

(58) Field of Classification Search
CPC ........... G01S 1/70; A61B 34/00; A61B 34/10; A61B 34/20; A61B 5/00; A61B 5/10; A61B 5/11; A61B 5/062; A61B 2034/2051; A61B 2034/2055; A61B 10/02; A61B 18/14
See application file for complete search history.

(56) References Cited

U.S. PATENT DOCUMENTS

| 8,768,621 | B2 | 7/2014 | Ruizenaar |
| 8,905,856 | B2 | 12/2014 | Parke et al. |
| 9,588,598 | B2 | 3/2017 | Li |
| 9,752,879 | B2 | 9/2017 | Al-Hamad et al. |
| 9,810,549 | B2 | 11/2017 | Johnson et al. |
| 2016/0377451 | A1 | 12/2016 | Pedrotti et al. |
| 2017/0074689 | A1 | 3/2017 | Lubberhuizen et al. |
| 2018/0059204 | A1 | 3/2018 | Mahfouz |
| 2019/0053858 | A1* | 2/2019 | Kapoor ................. A61B 34/20 |

* cited by examiner

*Primary Examiner* — Abdullahi Nur
(74) *Attorney, Agent, or Firm* — Fish & Richardson P.C.

(57) ABSTRACT

An electromagnetic tracking (EMT) system includes a tracked device, a tracking device, and a computing device. The EMT system is configured to receive, at the tracking device, an electromagnetic signal generated by the tracked device, determine, based on the electromagnetic signal, a set of possible positions and orientations of the tracked device relative to the tracking device, receive a measured inertial value representing a motion of the tracked device, determine an estimated inertial value corresponding to the motion of the tracked device based on at least one position and orientation of the set of possible positions and orientations, determine a difference value representing a difference between the estimated inertial value and the measured inertial value, determine a particular position and a particular orientation from the set in response to determining the difference value, and generate an output including the particular position and particular orientation.

22 Claims, 9 Drawing Sheets

From FIG. 4A

TRACKING AN OBJECT IN AN ELECTROMAGNETIC FIELD

TECHNICAL FIELD

This disclosure relates to tracking an object in a complex magnetic field, specifically determining a position and orientation of the object based on an electromagnetic (EM) signal and a inertial signal of an inertial measurement unit (IMU).

BACKGROUND

Electromagnetic Tracking (EMT) systems are used to aid location of instruments and anatomy in medical procedures, virtual reality (VR) settings, and augmented reality (AR) settings, among others. Such systems can determine a position of a sensor based on measured field lines of a transmitted magnetic field.

SUMMARY

An Electromagnetic Tracking (EMT) system can be used to track a device for a number of applications, such as for medical applications, AR/VR applications, and so forth. For example, in an AR/VR setting, the EMT system can be used to track the position and/or orientation of a device with respect to a head-mounted display (HMD) that is coupled to a user. The display of the HMD of the user can show a representation of the device in an AR/VR interface at an approximate position and orientation corresponding to an actual position and orientation of the device with respect to the user. For example, in a medical setting, the EMT system can determine the position and orientation of a surgical device with respect to an operator or other reference frame. Numerous additional applications for tracking an object are known.

The EMT system is configured to determine the position and orientation of a tracked device with respect to a receiver based on an electromagnetic (EM) signal (also referred to as a magnetic signal) emitted by an emitter of the tracked device. Position refers to a physical location of the emitter of the tracked device with respect to the receiver (or vice versa), and position data can be expressed as a position vector. Orientation refers to a direction the tracked device is facing with respect to the receiver, and can be expressed as an orientation matrix. The receiver is configured to demodulate the magnetic signal received from the emitter to obtain position data representing the position of the tracked device with respect to the receiver, and to obtain orientation data representing the orientation of the emitter with respect to the receiver. The magnetic signal received from an emitter of the EMT system is decomposed into a signal matrix. Elements of the signal matrix each have respective magnitudes that are a function of an amplitude of the received magnetic signal and a distance of the emitter from the receiver. In some implementations, the calculation of position and/or orientation can be performed in a coordinate space in the frame of the receiver (e.g., wherein the receiver represents the origin of the coordinate system). In some implementations, the calculation of position and/or orientation can be performed in a coordinate space in the frame of the emitter (e.g., wherein the emitter represents the origin of the coordinate system).

The magnetic signal includes two ambiguities that are resolved before the position data and the orientation data of the emitter and receiver can be determined. The first ambiguity includes a phase-lock loop (PLL) ambiguity. PLL ambiguity results in eight possible orientations of the emitter with respect to the receiver being represented in the magnetic signal (e.g., four right-handed solutions and four left-handed solutions, where "handed" refers to the configuration of the coordinate system). The second ambiguity includes a hemisphere ambiguity. Hemisphere ambiguity results in a representation in the magnetic signal of two possible positions of the emitter with respect to the receiver.

The EMT system described herein includes an inertial measurement unit (IMU) configured to provide inertial data of the emitter. The inertial data can include linear acceleration data measured by one or more accelerometers. The inertial data can include angular velocity data provided by one or more gyroscopes. While the IMU is described as coupled to the emitter for this example, the IMU can alternatively be coupled to the receiver.

The inertial data provided by the IMU is used by the EMT system to resolve the PLL ambiguity and the hemisphere ambiguity of the magnetic signal. For the PLL disambiguation, the EMT system computes (estimates) angular velocities for each of the four possible right-handed orientations of the emitter and compares them to a measured angular velocity included in the inertial data. The orientation associated with an estimated angular velocity having a positive correlation to the measured angular velocity is selected. For hemisphere disambiguation, a linear velocity and linear acceleration are estimated for each of the two possible positions of the emitter with respect to the receiver. The linear acceleration of the emitter is measured. The EMT system selects the position associated with an estimated linear acceleration that has a positive correlation to the measured linear acceleration.

The techniques described herein include one or more of the following advantages. The EMT system can determine a position and an orientation of the emitter with respect to the receiver without determining an initial position and/or orientation of the emitter with respect to the receiver (or vice versa). In some implementations, when an initial pose (e.g., initial position and initial orientation) of the emitter and/or tracker are known, the PLL ambiguity and the hemisphere ambiguity can be resolved based on determining a relative change in the magnetic signal with respect to the magnetic signal at the known initial position and initial orientation. However, the EMT system cannot always access an initial pose of the emitter and/or tracker. Correlating the inertial data of the IMU to the received magnetic signal provides a means to resolve the position and orientation ambiguities without a calibration step in which the EMT system confirms the initial state of the system. For example, a user need not confirm the approximate initial position and orientation of the emitter and/or transceiver when initializing use of the EMT system. Rather, the EMT system is configured to self-calibrate automatically upon commencement of tracking the emitter.

Additionally or in the alternative, the EMT system and techniques described in this disclosure improve system recovery from any faults, such as from a communication failure (e.g., loss of signal, dropped data, etc.), interference, or other such fault. Because the system does not require an initial position and/or orientation, the EMT system can reconnect and resume tracking without additional calibrations. For example, it is not required to initialize either the EM tracker or the IMU prior to commencement of tracking.

Additionally or in the alternative, the EMT system and techniques described in this disclosure do not require additional tracking systems (e.g. optical tracking systems).

In an aspect, the EMT system includes a tracked device. In some implementations, the tracked device includes an inertial measurement unit (IMU) configured to generate inertial data, and an emitter configured to generate an electromagnetic signal. In some implementations, EMT system includes a tracking device that includes a magnetic sensor configured to receive the electromagnetic signal from the tracked device; and a receiver configured to receive the inertial data from the tracked device. The EMT system includes a computing device including one or more processors. In some implementations, the computing device is configured to perform operations including determining a set of possible positions and orientations of the tracked device relative to the tracking device based on the electromagnetic signal. The operations include receiving a measured inertial value of the inertial data representing a motion of the tracked device. The operations include determining an estimated inertial value corresponding to the motion of the tracked device based on at least one position and orientation of the set of possible positions and orientations. The operations include determining a difference value representing a difference between the estimated inertial value and the measured inertial value. The operations include, in response to determining the difference value, determining a particular position and a particular orientation from the set of possible positions and orientations. The operations include generating an output comprising the particular position and the particular orientation.

In some implementations, for each frame in a series of frames, the difference value is determined for that frame, and the difference values are summed and compared to a threshold value.

In some implementations, the measured inertial value comprises a linear acceleration value. In some implementations, the measured inertial value comprises an angular velocity value.

In some implementations, the tracked device includes one or more input devices, the one or more input devices configured to generate input signals comprising instructions for the computing device, and the tracked device is configured to transmit the input signals to the computing device.

In some implementations, the electromagnetic signal corresponds to a first timestamp, and another electromagnetic signal received by the tracking device corresponds to a second timestamp representing a later time than the first timestamp.

In some implementations, the EMT system includes a base station configured to provide a second electromagnetic signal from a second emitter, and the base station is configured to provide reference frame for the tracked device and the tracking device. The particular position and the particular orientation are represented in coordinates of the reference frame.

In some implementations, determining the estimated inertial value includes generating a set of estimated inertial values, each estimated inertial value being based a pair of corresponding positions and orientations of the set of possible positions and orientations and another set of possible positions and orientations corresponding to a different measurement of the electromagnetic signal.

In some implementations, the difference value comprises a set of values, each value of the set corresponding to an axis of motion of the tracked device, and wherein the particular position and the particular orientation correspond to a set of values that are each positive.

In some implementations, the operations further include determining a gravitational component for the measured inertial value and correcting the measured inertial value based on the gravitational component.

In some implementations, the electromagnetic signal is represented as a 3×3 matrix of data.

In some implementations, the tracked device, the tracking device, and the computing device are a portion of one or more of a Virtual Reality (VR) system, an Augmented Reality (AR) system, a Mixed Reality (MR) system, and an extended reality (XR) system.

In some implementations, the tracking device is configured to couple to a head-mounted display (HMD).

In some implementations, the IMU comprises at least one accelerometer and at least one gyroscope.

In some implementations, the computing device is configured to perform the operations during an initialization phase of operation of the system.

In some implementations, the tracked device comprises a medical instrument.

In some implementations, the tracked device is represented in a graphical user interface at the particular position and the particular orientation relative to the tracking device.

In some implementations, the electromagnetic signal is modulated at a particular frequency that is associated with the tracked device, the particular frequency allowing the tracking device to identify the tracked device as the source of the electromagnetic signal.

In some implementations, the output comprises a timestamp associated with the particular position and the particular orientation.

In some implementations, the output comprises an identifier that identifies the tracked device as being associated with the particular position and the particular orientation.

In an aspect, a non-transitory computer readable medium stores instructions that are executable by one or more processors configured to perform operations including receiving, at a tracking device, an electromagnetic signal generated by a tracked device. The operations include determining, based on the electromagnetic signal, a set of possible positions and orientations of the tracked device relative to the tracking device. The operations include receiving, at the tracking device, a measured inertial value representing a motion of the tracked device. The operations include determining an estimated inertial value corresponding to the motion of the tracked device based on at least one position and orientation of the set of possible positions and orientations. The operations include determining a difference value representing a difference between the estimated inertial value and the measured inertial value. The operations include, in response to determining the difference value, determining a particular position and a particular orientation from the set of possible positions and orientations. The operations include generating an output comprising the particular position and the particular orientation.

In an aspect, a computer-implemented method includes operations for tracking a tracked device, the operations including receiving, at a tracking device, an electromagnetic signal generated by a tracked device. The operations include determining, based on the electromagnetic signal, a set of possible positions and orientations of the tracked device relative to the tracking device. The operations include receiving, at the tracking device, a measured inertial value representing a motion of the tracked device. The operations include determining an estimated inertial value corresponding to the motion of the tracked device based on at least one position and orientation of the set of possible positions and orientations. The operations include determining a difference value representing a difference between the estimated inertial value and the measured inertial value. The operations include, in response to determining the difference value, determining a particular position and a particular orientation from the set of possible positions and orientations. The operations include generating an output comprising the particular position and the particular orientation.

The details of one or more embodiments of the subject matter described herein are set forth in the accompanying drawings and the description below. Other features, objects, and advantages of the subject matter will be apparent from the description and drawings, and from the claims.

DESCRIPTION OF DRAWINGS

Like reference symbols in the various drawings indicate like elements.

DETAILED DESCRIPTION

An Electromagnetic Tracking (EMT) system can be used in medical settings, virtual reality (VR) settings, augmented reality (AR) settings, a Mixed Reality (MR) system, an extended reality (XR) system, etc., to track a device. For example, in a surgical setting, the EMT system can be used to track medical equipment, robotic arms, etc., thereby allowing the three-dimensional position (e.g., location) and the orientation of the device to be known to a medical professional (e.g., a surgeon) during a medical procedure.

A magnetic signal can represent a position and an orientation of a device. The position and the orientation represented in the magnetic signal can be ambiguous, meaning that there are several possible positions and/or orientations corresponding to the received magnetic signal. To provide a means for a computing device to disambiguate the position and the orientation of the device represented in the magnetic signal, further data that contextualizes the position data and the orientation data are provided in the form of inertial data (e.g., motion data) that is associated with the position and orientation of the device at a given time. A computing device can use the inertial data to disambiguate the position and the orientation to determine the true position and orientation of the tracked device in the environment of the EMT system. The initial position and orientation of the tracked object in the system need not be known.

Figure 1A:
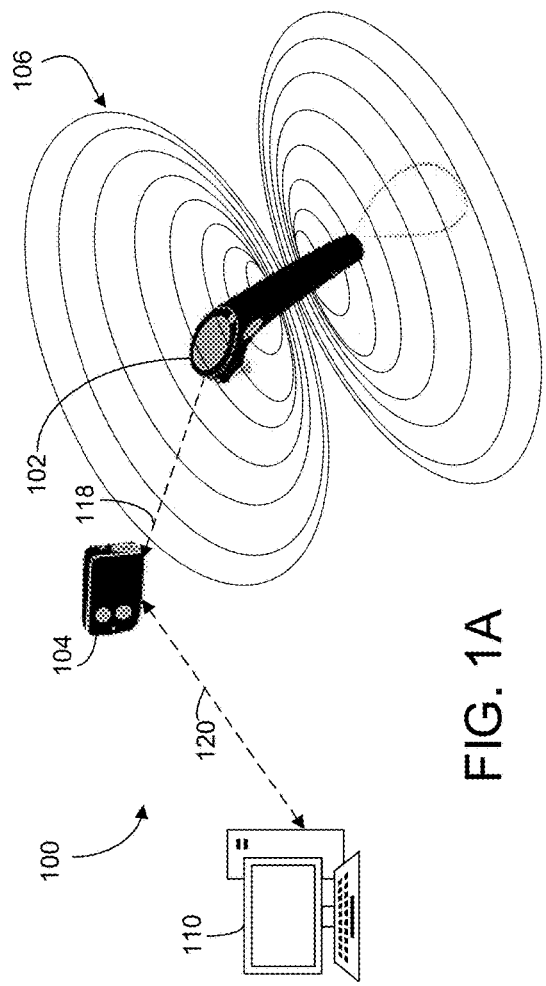
FIG. 1A shows a schematic diagram of an example Electromagnetic Tracking (EMT) system that includes a magnetic signal emitter, a magnetic signal receiver, and base station.
Figure 1C:
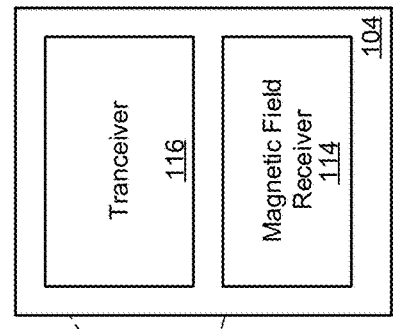
FIG. 1C shows an example of a tracking device comprising a magnetic field receiver.
Figure 1B:
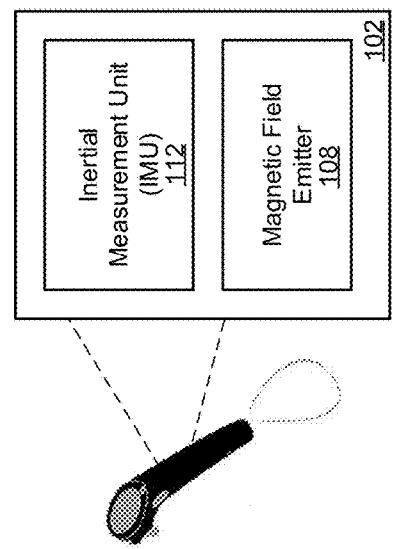
FIG. 1B shows an example of a tracked device comprising a magnetic field emitter and an inertial measurement unit.

FIG. 1A shows an exemplary embodiment of an electromagnetic tracking (EMT) system 100, which can be used for tracking a tracked device 102 of FIG. 1B by a tracking device of FIG. 1C. The system 100 is configured to determine a relative location of the tracked device 102 with respect to a tracking device 104. In general, the tracked device 102 of the system 100 includes a magnetic field emitter 108 that is configured to generate a magnetic field 106, such as by one or more field-emitting coils. The tracking device 104 of the system 100 includes a magnetic field receiver 114 that is configured to measure characteristics of the magnetic field 106, such as by one or more field-measuring coils. The tracked device 102 includes an inertial measurement unit (IMU) 112 configured to generate inertial data based on movement of the tracked device 102. The tracking device 104 includes a transceiver 116 for receiving the inertial data from the tracked device 102.

In some implementations, the tracking device 104 is configured to measure characteristics of the magnetic field 106 and provide the measurements to a computing device 110. The computing device 110 is configured to determine information related to the tracked device (e.g., one or both of position and orientation information) based on the measurements. In some implementations, the computing device 110 can be a portion of the tracking device 104. In some implementations, the computing device can be another device separate from the tracking device. In some implementations, the magnetic field emitter 108 includes emitting coils 108 (sometimes referred to as field coils) and the magnetic field receiver 114 includes field measuring coils (sometimes referred to as pick-up coils).

The EMT system 100 is configured to determine the position and orientation of the tracked device 102 with respect to a receiver based on an electromagnetic (EM) signal 106 (also referred to as a magnetic signal 106) emitted by the emitter 108 of the tracked device 102. The position of the tracked device 102 includes a physical location of the emitter 108 of the tracked device 102 with respect to the receiver 114 of the tracking device 104 (or vice versa). In some implementations, position data can be expressed as a position vector of position coordinates (e.g., x, y, z coordinates). While position can be represented as coordinates in the frame of the tracked device 102 where the tracked device 102 is the origin, position can alternatively be represented as a coordinates in the reference frame of the receiver 114, in which the receiver is the origin.

The orientation of the tracked device 102 refers to a direction the tracked device is facing with respect to the tracking device 104, and can be expressed as an orientation vector of coordinates (e.g., azimuth ($\psi$), altitude ($\theta$), and roll ($\varphi$) angles). In some implementations, the orientation can be represented as roll, pitch, and yaw angles, representing rotation about the z, y, and x axes, respectively. In some implementations, the orientation data can be represented as an orientation quaternion, orientation vector, orientation matrix, etc. While orientation can be represented as coordinates in the frame of the tracked device 102 where the tracked device 102 is the origin, orientation can alternatively be represented as a coordinates in the reference frame of the receiver 114, in which the receiver is the origin. In this way, the tracked device 102 may act as a six degree of freedom (6DoF) sensor that is configured to allow for measurement of position and orientation information related to a forward/back position, up/down position, left/right position, azimuth, altitude, and roll.

In some implementations, a base station (not shown) is included in EMT system 100. The base station is similar to the tracked device 102, but is stationary during operation of the EMT system 100. The purpose of the base station is to be a global reference frame simply by being static during use of the system.

Turning to FIG. 1B, the tracked device 102 includes the emitter 108 and the inertial measurement unit (IMU) 112 configured to provide inertial data representing motion of the tracked device 102. Typically, the inertial data represents motion of the tracked device 102 relative to a fixed device of an environment of the system 100 (e.g., global acceleration values such as gravity can be corrected inertial data by incorporating a gravity estimate). The inertial data can include linear acceleration data measured by one or more accelerometers. The inertial data can include angular velocity data provided by one or more gyroscopes.

In some implementations, the tracked device 102 includes a device that manipulated in an environment of the system 100, e.g., by a user of the system 100. For example, the tracked device 102 can include one or more of a controller for VR/AV applications, a surgical instrument, etc. In some implementations, the tracked device 102 can be relatively stationary relative to a device that is manipulated in the environment. For example, the tracked device 102 can include a computing system, a head-mounted display (HMD), etc. that is relatively stationary relative to the tracking device 104. In such applications, the IMU 112 can be affixed to the tracking device 104 rather than the tracked device 102. In other words, the emitter 108 can be a part of the tracked device 102 or the tracking device 104, while the receiver 114 can be part of the tracking device 104 or the tracked device 102, respectively, while the IMU 112 is generally affixed to the device that is configured to move during operation of the system.

Turning to FIG. 1C, the tracking device 104 includes the receiver 114 for measuring the magnetic signal 112 and a transceiver (e.g., a transmitter-receiver pair of devices). The transceiver 112 includes an antenna and is configured to receive inertial data from the IMU 112 of the tracked device 102 by a communication channel 118 (e.g., over a wireless communication channel). The inertial data can be transmitted from the tracked device 102 to the tracking device 104 by communication protocols such as Bluetooth, WiFi, ZigBee, etc. In some implementations, the tracking device 104 is coupled to a head-mounted display (HMD) configured to couple to a user and provide a graphical user interface to the user. In some implementations, the tracking device 104 is coupled to (or otherwise a part of) a computing system 110 configured to perform the calculations for determining the position and the orientation of the tracked device 102 for the system 100.

Returning to FIG. 1A, the computing device 110 comprises one or more processors and is configured to receive the position data, the orientation data, and the inertial data that are measured and/or received by the tracking device 104. In some implementations, the tracking device 104 measures the magnetic signal 112 emitted by the tracked device 102 and converts the magnetic signal into position data and orientation data that can be processed by the computing device 110. In some implementations, the tracking device 104 is a part of the computing system 110. In some implementations, the tracking device 104 transmits the position data, inertial data, and orientation data to the computing device 110 by a communication channel 120. The communication channel 120 can include a wireless communication channel, wired communication channel, or a combination of both. In situations where the tracking device 104 is a part of the computing device 110, the description can refer to the computing device and the tracking device interchangeably as disambiguating the position data and the orientation data.

The computing device 110 is configured to determine one or both of the position and the orientation of the tracked device 102 based on the received magnetic signal 112 representative of the measured characteristics of the magnetic field. In some examples, the computing device 110 may determine the position and/or orientation of the tracked device 102 relative to the position and/or orientation of the tracking device 104, the position and/or orientation of the emitter 108, the position and/or orientation of the receiver 114, etc.

In some implementations, the tracking device 104 is configured to demodulate the magnetic signal 106 received from the emitter 108 to obtain position data representing the position of the tracked device 102 with respect to the tracking device 104, and to obtain orientation data representing the orientation of the tracked device 102 with respect to the tracking device 104. In some implementations, the magnetic signal 106 is associated with a particular frequency that the tracking device 104 can associate with the tracked device 102 to distinguish the tracked device from one or more other devices that may be emitting magnetic signals at other frequencies. The tracking device 104 can tag the position data, orientation data, and inertial data received from the tracked device 102 with a device identifier. The computing device 110 can determine which device the position data, orientation data, and inertial data are associated with based on the identifier, and use this information for one or more applications. For example, the computing device may generate a user interface in which the tracked device 102 is being represented along with other tracked devices. For example, the position and orientation of the tracked device 102 are reported, etc.

Figure 2:
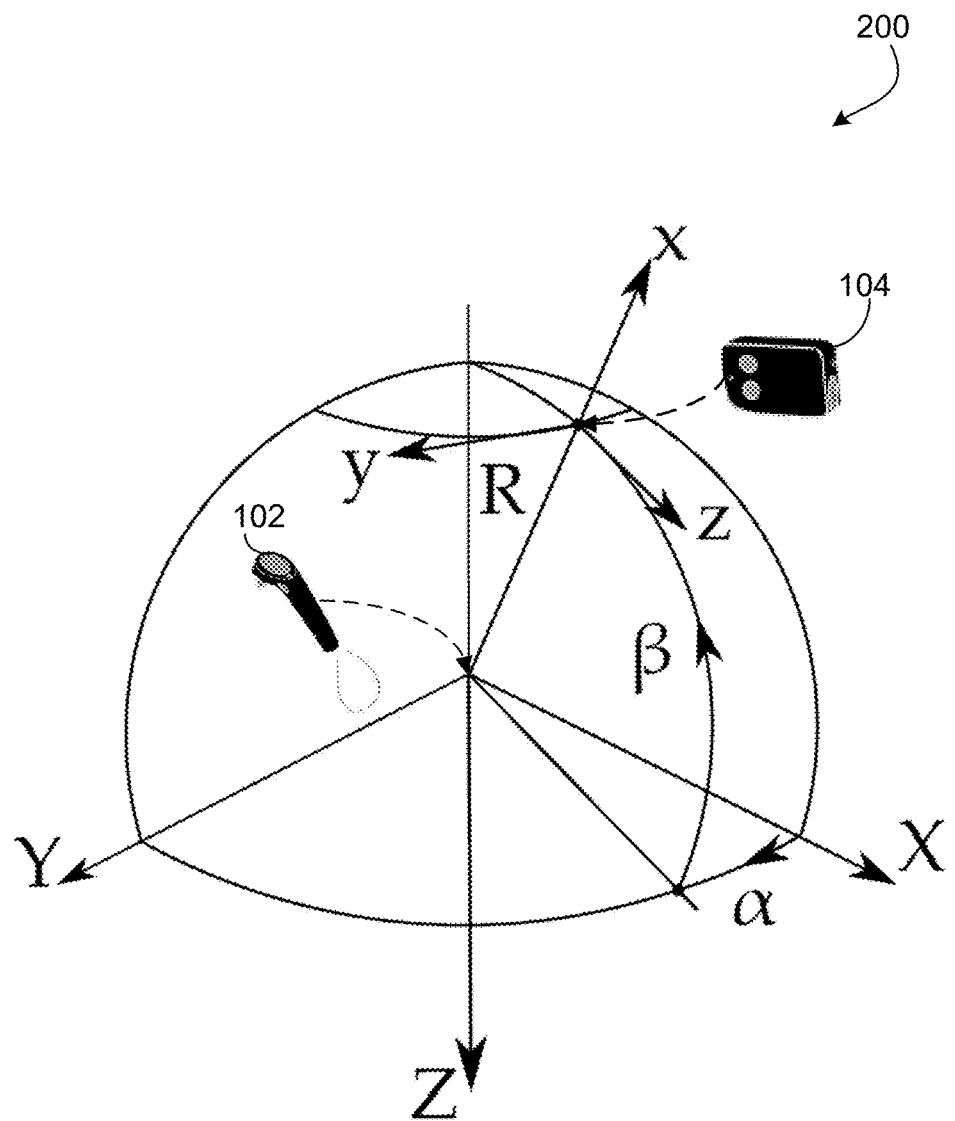
FIG. 2 shows an example of a coordinate system in a frame of the tracked device.

Turning to FIG. 2, an example coordinate system 200 is shown for tracking the tracked device 102 by the tracking device 104. In the coordinate system 200, the tracked device 102 represents the origin of the coordinate system including position coordinates (e.g., x, y, z coordinates) and orientation coordinates (e.g., azimuth ($\psi$), altitude ($\theta$), and roll ($\varphi$) angles). In FIG. 2, a z-axis dipole system of the emitter of the tracked device 102 is shown with a coordinate frame marked by coordinates X, Y, and Z and a tracking device 104 frame with coordinates labeled x, y, and z. The coordinate R represents the distance between the tracked device 102 and the tracking device 104.

The tracking device 104 decomposes the magnetic signal 106 received from the emitter 108 of the EMT system into a signal matrix. Elements of the signal matrix each have respective magnitudes that are a function of an amplitude of the received magnetic signal 106 and a distance of the emitter 108 from the receiver 114. In some implementations, the calculation of position and/or orientation of the tracked device 102 can be performed in a coordinate space in the frame of the receiver (e.g., wherein the receiver represents the origin of the coordinate system). In some implementations, the calculation of position and/or orientation can be performed in a coordinate space in the frame of the emitter (e.g., wherein the emitter represents the origin of the coordinate system). For this example, position and orientation are shown in the frame of the tracked device 102.

The magnetic signal includes two ambiguities that are resolved before the position data and the orientation data of the emitter and receiver can be determined. The first ambiguity includes a phase-lock loop (PLL) ambiguity. PLL ambiguity results in four possible orientations of the emitter with respect to the receiver being represented in the magnetic signal. The second ambiguity includes a hemisphere ambiguity. Hemisphere ambiguity results in a representation in the magnetic signal of two possible positions of the emitter with respect to the receiver.

The demodulation process is assisted by PLL processing logic with, typically, no synchronization between the signal generated at the transmitter coils and the reference signal generated at the receiver module. Generally this lack of synchronization causes the signs of the magnitude values of the magnetic signal 106 to be ambiguous as described above. In some implementations, the magnetic signal 106 can be decomposed into position and orientation data (represented by signal matrices) according to the following:

$$S = kAP^T CP \quad (1)$$

where S is the signal matrix, k is the attenuation factor, A is the orientation or attitude matrix, P is the position or tracking matrix, and C is a constant matrix that defines the coupling coefficients of a three-coil arrangement. The tracking matrix P can be defined as follows:

$$P = \begin{bmatrix} \cos(\alpha)\cos(\beta) & \sin(\alpha)\cos(\beta) & -\sin(\beta) \\ -\sin(\alpha) & \cos(\alpha) & 0 \\ \cos(\alpha)\sin(\beta) & \sin(\alpha)\sin(\beta) & \cos(\beta) \end{bmatrix} \quad (2)$$

where $\alpha$ and $\beta$ partially determine the position of the receiver 114 in the frame of the emitter 108 in spherical coordinates. It follows that $$\alpha = \tan^{-1}\frac{y}{x} \quad (3)$$

$$\beta = \sin^{-1}\frac{-z}{r} \quad (4)$$

where r is the receiver to transmitter distance. When decomposing S into its component matrices, the values of $\alpha$ and $\beta$ can be determined once the ambiguous signs of the values of x and y are resolved.

The signs of the magnitudes of the magnetic signal 106 represented by the signal matrix are ambiguous when received, but the signs are not each independent of one another. For example, the magnitudes on the same column of the signal matrix include a same sign change for each potential position and orientation solution. This means that only three signs need to be resolved, which yields eight sign combinations. Furthermore, four of the sign combinations produce a left-handed coordinate system including duplicative potential positions and orientation solutions. Thus, the solution space includes four possibilities.

The ambiguous PLL signs have an effect on both position and orientation because these are at the signal level from which all is computed. Hemisphere ambiguity on the other hand only affects position. Generally, the EMT system is configured to first resolve PLL ambiguity, followed by hemisphere ambiguity.

In some implementations, when determining position from the magnetic signal 106, the computing system 110 generates an intermediary signal matrix that is related to P, and the computing system determines the axis of rotation by eigenvector decomposition. This is in the alternative to determining the position from $\alpha$ and $\beta$, and directly from P.

Recall that P is a 2-DOF rotation matrix in spherical coordinates. Therefore, the axis of rotation of P is collinear with the position vector of the receiver 114 in the frame of the emitter 108. By determining position this way, the position vector is constrained to the axis of rotation of P, which can only be on one of two sides of the origin. This reduces hemisphere ambiguity to a single sign. Thus, the computing device 110 can either leave alone the result of the eigenvector decomposition or negate it.

The inertial data provided by the IMU 112 is used by the computing device 110 of the EMT system 100 to resolve the PLL ambiguity and the hemisphere ambiguity of the magnetic signal. For the PLL disambiguation, the EMT system computes (estimates) angular velocities for each of the four possible orientations of the emitter and compares them to a measured angular velocity included in the inertial data. The orientation associated with an estimated angular velocity having a positive correlation to the measured angular velocity is selected. For hemisphere disambiguation, a linear velocity and linear acceleration are estimated for each of the two possible positions of the emitter with respect to the receiver. The linear acceleration of the emitter is measured. The EMT system selects the position associated with an estimated linear acceleration that has a positive correlation to the measured linear acceleration. The details of both PLL disambiguation and hemisphere disambiguation using the inertial data are described below in reference to FIGS. 5-8.

Figure 3:
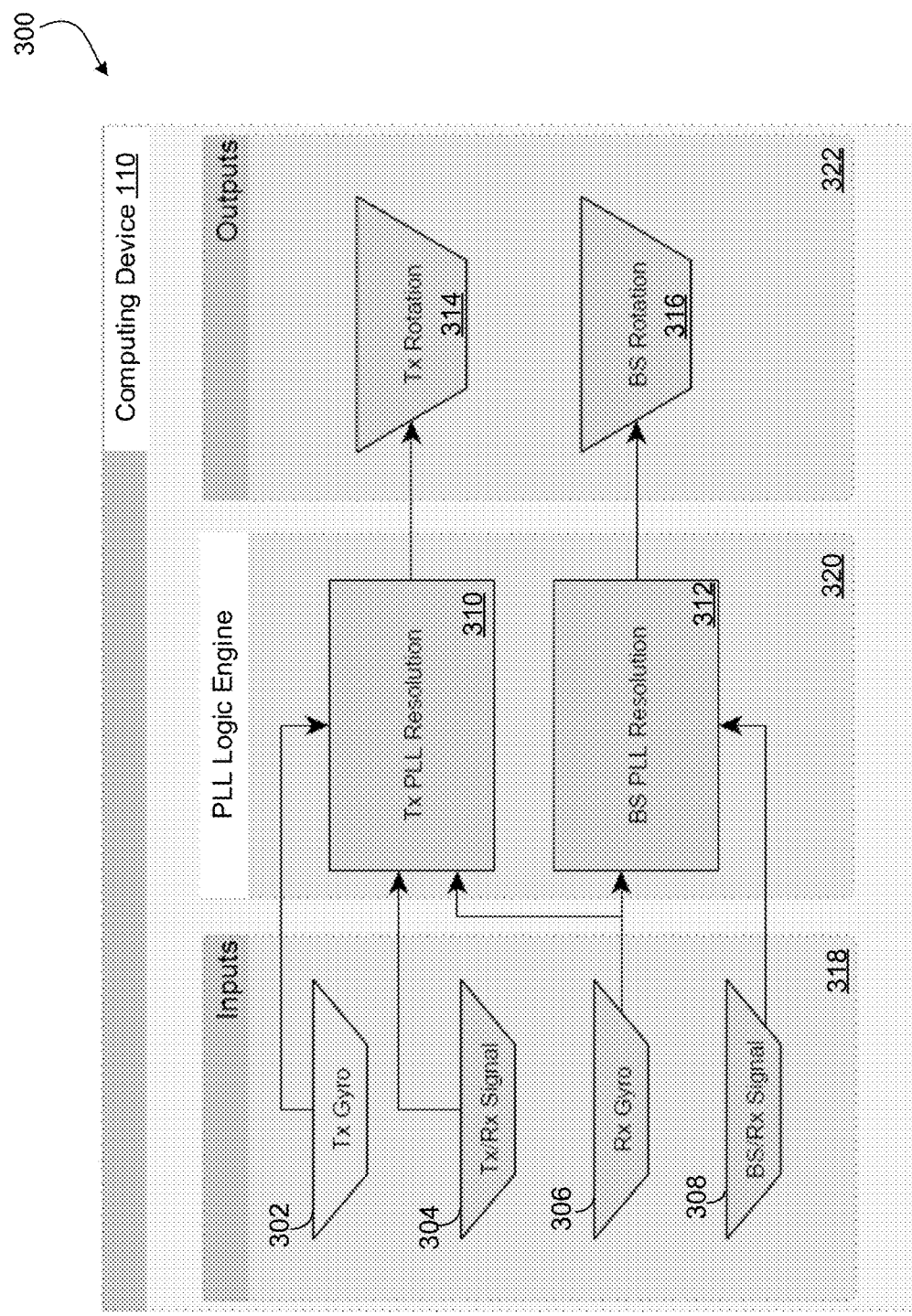
FIG. 3 shows a dataflow diagram showing an example of dataflow for PLL disambiguation for tracking an object in an electromagnetic field.

FIG. 3 shows a dataflow diagram showing an example of dataflow for PLL disambiguation for tracking an object in an electromagnetic field for a system 300. The system 300 includes a base station and a tracked device that each emit magnetic field signals that are received by the computing device 110. In some implementations, the base station provides a "world frame" for the tracked device 102 and the computing device 110.

The computing device 110 is configured to receive inputs 318 at a PLL logic engine 320. The inputs include an IMU input 302 from the tracked device 102, a magnetic signal 304 from the tracked device 102, an IMU input 306 from the base station, and a magnetic signal 308 from the base station.

The PLL logic engine 320 is configured to perform PLL disambiguation (resolution) for each of the tracked device 102 and the base station. The PLL disambiguation for the tracked device 102 can be performed at module 310, and the PLL disambiguation for the base station can be performed at module 312. In some implementations, the modules 310, 312 operate in parallel. In some implementations, the modules 310, 312 operate in series and can use the same hardware. The PLL disambiguation is performed as described below in relation to processes 500, 600, and 700 of FIGS. 5-7.

The outputs 322 of the PLL disambiguation of the PLL logic engine 320 include the orientation data 314 of the tracked device 102 and the orientation data 316 of the base station.

Figure 4A:
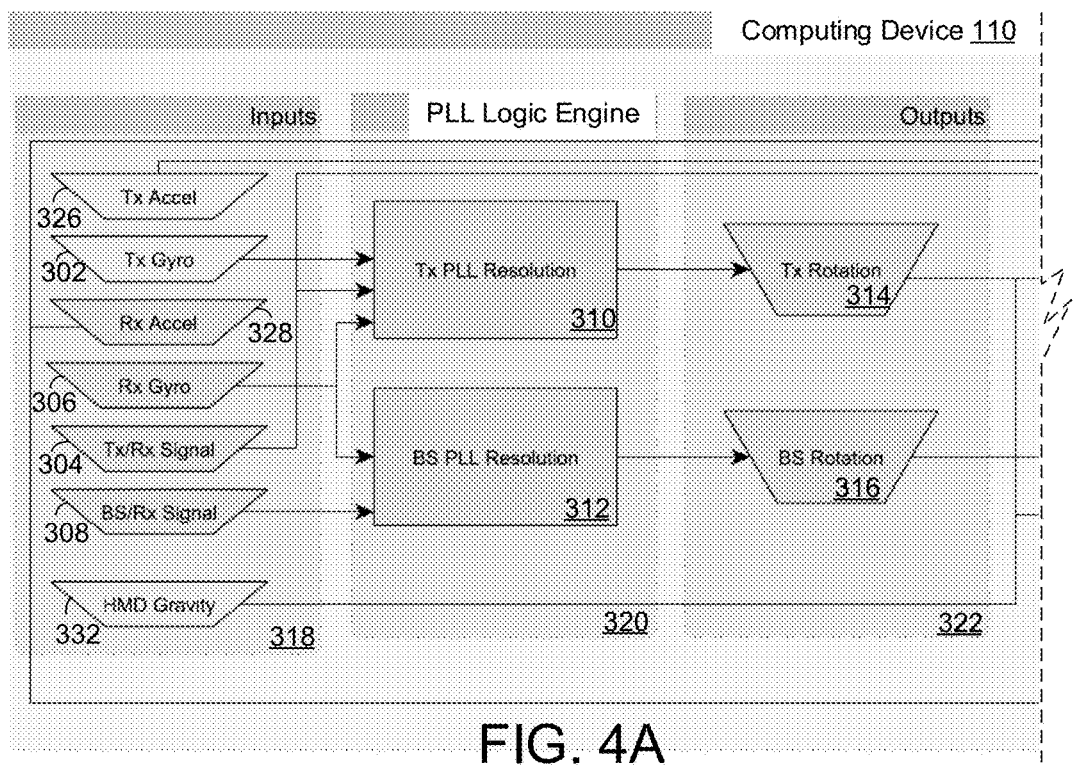
FIGS. 4A-4B shows a dataflow diagram showing an example of dataflow for hemisphere disambiguation for tracking an object in an electromagnetic field.
Figure 4B:
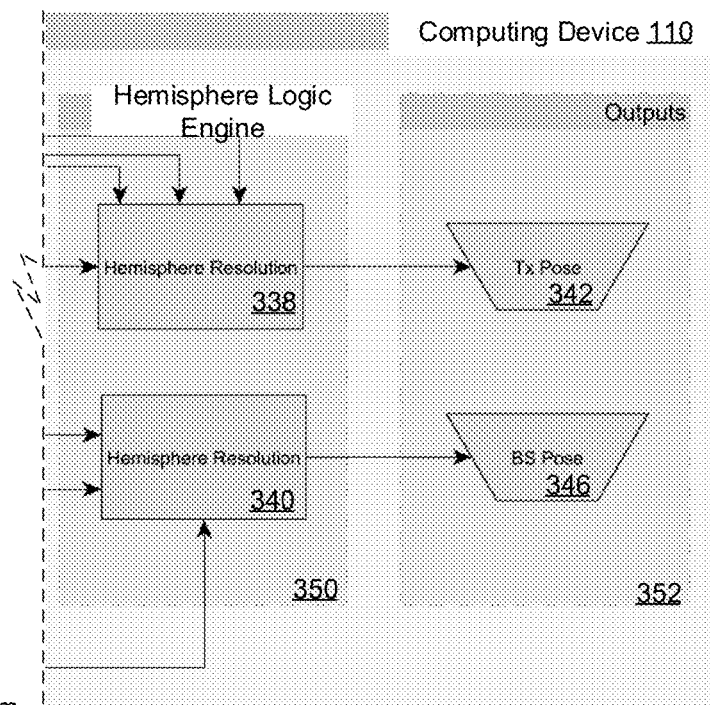

FIGS. 4A-4B shows a dataflow diagram showing an example of dataflow for hemisphere disambiguation for tracking an object in an electromagnetic field. As described above in relation to FIG. 3, the system 300 of FIG. 4A-4B includes a base station and a tracked device (e.g., tracked device 102 of FIGS. 1A-1B). As described above, the PLL logic engine 320 is configured to perform PLL disambiguation using the modules 310, 312 for each of the tracked device 102 and the base station, respectively. Module 310 receives inertial data 302 from the tracked device 102, inertial data 306 from the base station, and the magnetic signal 304 from the tracked device 102 for computing the PLL disambiguation. Module 312 receives inertial data 306 from the base station and the magnetic signal 308 from the base station. The PLL logic engine 320 generates outputs 322 that can be used for hemisphere disambiguation. Module 310 outputs a tracked device 102 orientation data 314, and module 312 outputs a base station orientation data 316.

More detail regarding the generation of outputs 314, 316 is described in relation to FIGS. 5-7, below.

In some implementations, the outputs 322 including the disambiguated orientation data are received by a gravity logic engine (not shown) of the computing device 110. The gravity logic engine is configured to adjust the orientation outputs 314, 316 to correct for a gravity component. The gravity component can be based on a world frame that is known from the base station, which is configured to remain approximately stationary during operation of the system. A gravity estimation module (not shown) can receive the orientation data 314, 316, and the inertial data 302, 332 to estimate the gravity component of the orientation data 314, 316 and correct the orientation data as needed. The correction for the gravity component is described in further detail below with respect to FIGS. 6-8. In some implementations, the orientation data 314, 316 is corrected based on the estimated gravity component.

Figure 8:
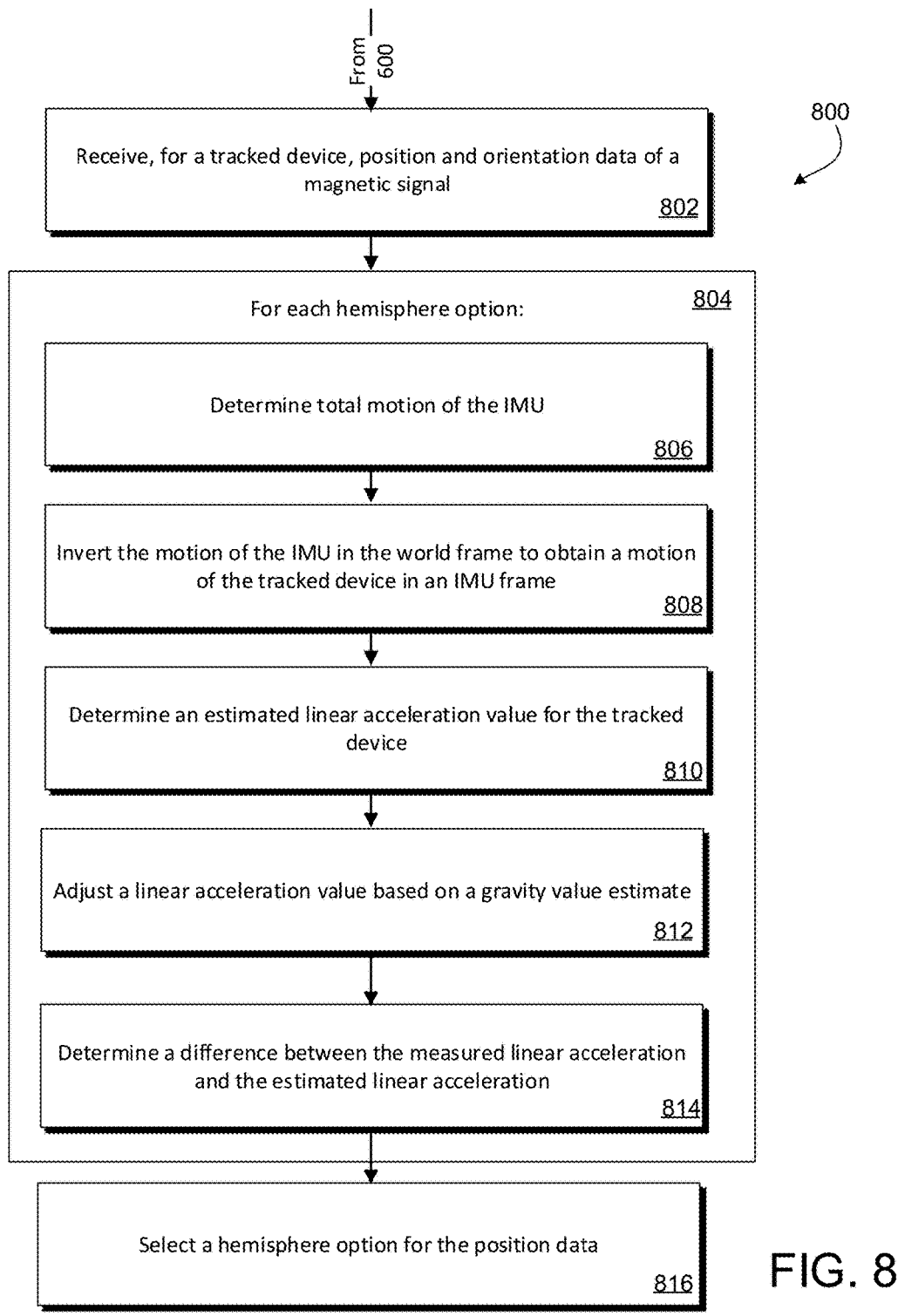

Turning to FIG. 4B, the hemisphere logic engine 350 of the computing device 110 is configured to perform hemisphere disambiguation as described below in relation to FIGS. 5 and 8. The hemisphere logic engine 350 is configured to receive the magnetic signal 308 of the base station, the magnetic signal 304 of the tracked device 102, the estimated gravity component (if applicable), the base station linear acceleration value 328, and the tracked device 102 linear acceleration value 326. Specifically, a tracked device 102 hemisphere disambiguation module 338 is configured to receive the acceleration data 326, 328, magnetic signal 304, and a measured gravity component 332. Additionally, a base station hemisphere disambiguation module 340 is configured to receive the acceleration value 328, the base station magnetic signal 308, and the gravity component. Each of modules 338, 340 can operate in parallel or in series. In some implementations, the modules 338, 340 can operate using the same hardware (e.g., a part of the computing device 110). Module 338 is configured to output the position and orientation data (pose 342) for the tracked device 102, and module 340 is configured to output the orientation and position data (pose 346) for the base station (e.g., a "world frame"). Pose 342 and pose 346 are outputs 352 of the computing device 110 and can be used for any number of applications.

Figure 5:
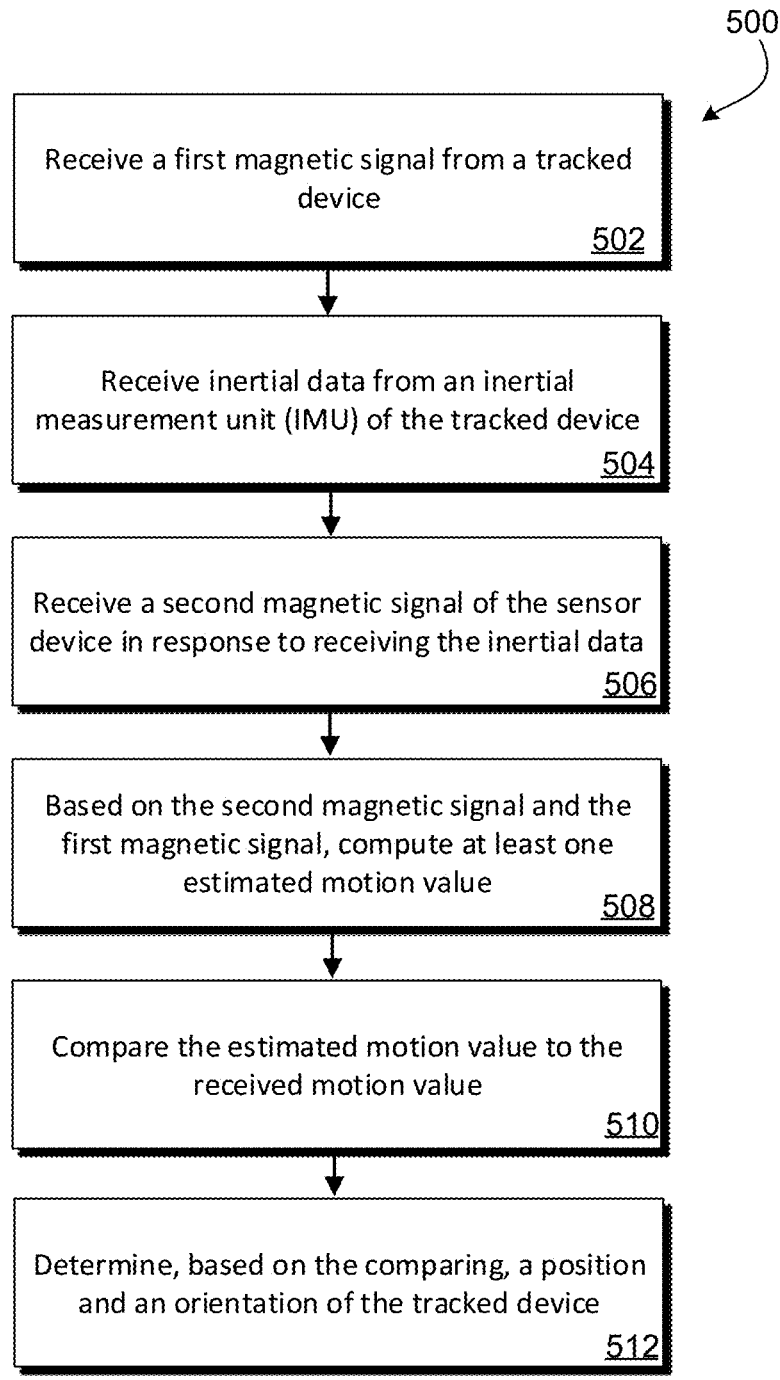
FIGS. 5-8 show example flow diagrams of a process for tracking an object in an electromagnetic field.

FIG. 5 shows a flow diagram of a process 500 for tracking an object in an electromagnetic field. The process 500 can be performed by a computing system such as computing system 110 of the EMT system 100 of FIGS. 1A-1C.

The computing system 110 receives (502) a first magnetic signal representing a position of an object (e.g., tracked device 102 of FIGS. 1A-1B) relative to a measuring device in a magnetic field (e.g., magnetic field 106). The tracked device 102 is configured to generate the magnetic signal, which is measured by a tracking device (e.g., tracking device 104 of FIG. 1A, 1C). The magnetic signal can be processed by processing device of the tracking device 104 once the signal is measured by the receiver 114 to generate position data and orientation data. In some implementations, a digital representation of the signal is sent to the computing device 110 for processing. As stated above, in some implementations, the tracking device 104 is a part of the computing device 110.

The first magnetic signal represents a first position of the tracked device 102 relative to the tracking device 104. The magnetic signal is decomposed into a signal matrix as described above in relation to FIG. 2. For example, the magnetic signal is decomposed (e.g., by the computing device 110) into the signal matrix of equation 2. The magnitude and direction of the magnetic field at the tracking device 104 are used to determine the values of the x, y, z, and r coordinates of the signal matrix. As described above, the signs of the matrix elements cannot be determined from the first magnetic signal alone. Rather, there are four possible orientations and two possible positions represented in the signal matrix of the first magnetic signal. In some implementations, the signal matrix generated by the computing system 110 is stored (e.g., cached in memory) for later use.

The first magnetic signal can be measured by the tracking device 104 in response to a system initialization, such as a request for tracking data from the computing device. In some implementations, the tracking device 104 and the tracked device 102 are configured to handshake upon initialization to establish communication of data (e.g., to establish communication channel 118), and the tracking device 104 can measure the magnetic signal upon completion of the handshake process. In some implementations, the tracking device 104 measures the first magnetic signal in response to a user input, such as press of a button on the tracked device 102 or other input device of the EMT system 100. In some implementations, the first magnetic signal includes one of a plurality of magnetic signals that are measured periodically by the tracking device and stored in memory. Other such triggers for measuring the first magnetic signal are possible.

The computing system is configured to receive (504) inertial data from an IMU coupled to the tracked device 102. As described above, in some implementations, the IMU can be coupled to the tracking device 104 that is moving through the magnetic field generated by the tracked device 102, and the frame of the coordinate system represents the tracked device 102 rather than the tracking device 104.

The inertial data can be sent from the tracked device 102 to the tracking device 104 in response to detecting that the IMU is producing valid data, that acceleration values captured by the IMU exceed a minimum threshold (e.g., indicating that the tracked device 102 is moving), in response to a request for data from the tracking device 104 over channel 118, and so forth. For example, the tracking device 104 can measure a magnetic signal at a particular time ti and subsequently request inertial data from the tracked device 102 corresponding to time ti. In some implementations, the tracked device 102 broadcasts inertial data at time intervals, and the tracking device 104 measures the magnetic signal in response to receiving the inertial data at a particular time.

As described above, the inertial data include data representing the linear accelerations and the angular velocities of the tracked device 102. In some implementations, the linear accelerations can be measured by accelerometer(s) of the IMU 112, and the angular velocities can be measured by the gyroscope(s) of the IMU. Once inertial data are received by the computing device 110, the receiver 114 measures a second magnetic signal. In some implementations, the second magnetic signal is associated with a timestamp representing a time that is approximately contemporaneous with measurement of the inertial data by the IMU 112. The second magnetic signal represents a second position of the tracked device 102 relative to the tracking device 104.

The computing device 110 is configured to estimate (508) a motion of the tracked device 102 based on the first magnetic signal and the second magnetic signal. As stated above, there are several possible orientations of the tracked device 102 and multiple possible positions of the tracked device 102 for each of the first and second magnetic signals. The computing device 110 is configured to determine, for each possible pairing of orientations and for each possible paring of positions from the first and second magnetic signals, expected inertial data that would be received if the selected pair of orientations and positions (an orientation and position selected from each of the first and second magnetic signals) represent the actual orientations and positions of the tracked device 102 when the first magnetic signal and the second magnetic signal are measured, respectively.

For example, the first magnetic signal is associated with possible orientations $A_1$, $B_1$, $C_1$, and $D_1$, corresponding to four right-handed solutions for the orientation matrix A of equation 1. Here, single coordinates are used for simplicity of explanation, but in practice, each orientation and position is represented by position and orientation coordinates as described above. Additionally, the second magnetic signal is associated with possible orientations $A_2$, $B_2$, $C_2$, and $D_2$, corresponding to four right-handed solutions for the signal matrix P of FIG. 2. For each pair of possible orientations $(A_1, A_2; B_1, B_2; C_1, C_2; D_1, D_2)$ a motion vector is estimated representing the expected angular velocities for moving from the first orientation to the second orientation over the time ti of the first magnetic signal and the time to of the second magnetic signal.

A similar process occurs for the two possible positions of the tracked device 102. The first magnetic signal is also associated with possible and positions X1 and Y1, corresponding to a first and second hemisphere solution, respectively. The second magnetic signal is also associated with possible and positions X2 and Y2. Each position pair $(X_1, X_2; Y_1; Y_2)$ is used by the computing device 110 to determine expected linear acceleration values associated with the second position based on motion of the tracked device 102 between the first position represented by the first magnetic signal and the second position represented by the second magnetic signal. Because at least two position values are used by the EMT system 100 to estimate linear velocity, and at least two linear velocities are used by the EMT system to estimate liner acceleration, the EMT system uses at least three position values to estimate linear acceleration values.

Once the inertial data including the expected linear accelerations and expected angular velocities are determined for each possible pair of coordinates represented in the first and second magnetic signals, the computing device 110 compares (510) the expected inertial data to the measured inertial data received from the IMU 112. In this way, a comparison is being performed in an inertial space rather than a pose space including the orientations and the positions. In other words, a pose of the IMU 112 is not estimated directly from the IMU data, but rather a comparison of the estimated inertial data to the measured inertial data is performed.

The comparison of the estimated (expected) inertial data to the measured inertial data can include a distance between the values of the estimated and measured inertial data. The correct pair of possible orientation coordinates (e.g., $A_1, A_2$; $B_1, B_2$, etc.) and possible position coordinates $(X_1, X_2; Y_1, Y_2)$ is generally associated with the smallest distance to the measured inertial data. The potential coordinates (both position and orientation) associated with the smallest difference between their associated expected inertial data and the measured inertial data can be selected by the computing device 110 as representing the actual position and orientation of the tracked device 102.

In some implementations, noisy data can result in the incorrect set of coordinates being selected by the computing device 110 as representing the actual pose of the tracked device 102. Additionally, because the incorrect coordinates are associated with a signal that is out of phase from the true signal, for a single measurement, the computing device 110 can compute small distances for several pairs of coordinates or similar distances for several pairs of coordinates.

To resolve these potential issues, the computing device 110 can repeat this process over several iterations of received first and second magnetic signals. In some implementations, the second magnetic signal of a first iteration becomes the first magnetic signal of a second iteration. The distances that are determined by the computing device 110 for each pair of possible coordinates can be compared to a threshold tolerance. If the difference between the signals is less than threshold, the frame is considered correlated and a counter is incremented. The counter can be incremented over the plurality of iterations that indicate correlation.

In some implementations, a cumulative sum of the measured and estimated values and the measured values of the angular velocities in each of the x, y, and z axes can be generated. A positive correlation is found when the sum exceeds a threshold value for all three axes. For each incorrect solution, fewer than all three axes will be associated with a positive cumulative sum. For example, zero, one, or two of the axes may yield a positive cumulative sum over a threshold number of frames of measured magnetic signals.

Once the cumulative sum associated with a particular pair of coordinates exceeds a threshold, the computing device 110 can select that particular pair of coordinates as representing the true pose of the tracked device 102. If a pair of coordinates is associated with a distance between the expected inertial data and the measured data that exceeds the threshold tolerance the cumulative sum can be reset to zero. Eventually, each of the incorrect pairs of coordinates will be associated with estimated inertial data that is out of phase with the measured inertial data, and the counter for that pair of coordinates is reset. Only the coordinates associated with the actual pose of the tracked device 102 will have estimated inertial data that correlates sufficiently with the measured inertial data over enough iterations for the cumulative sum to exceed the threshold. In some implementations, the threshold can include 10 frames (iterations), 20 frames, 50 frames, 100 frames, etc. In some implementations, the frames are consecutive. In some implementations, the threshold can include a tolerance of a specified number of frames that do not meet the threshold as a moving percentage to account for noisy data. Other variations of these thresholding approaches are possible.

When the cumulative sum for a particular pair of coordinates exceeds a threshold (e.g., the pair of coordinates are associated with expected inertial data that correlates to the actual inertial data for more than the threshold number of consecutive frames), the particular pair of coordinates is selected by the computing device 110 as representing the pose of the tracked device 102. Once this determination is made by the computing device 110, the computing device need not continue the process, as the signs of the signal matrix are chosen and the signal is disambiguated (and accurate pose data can be determined). However, the computing device 110 may periodically repeat this test during operation of the EMT system 100 to ensure that the selected pair of coordinates still correlates to the actual pose of the tracked device 102.

Figure 6:
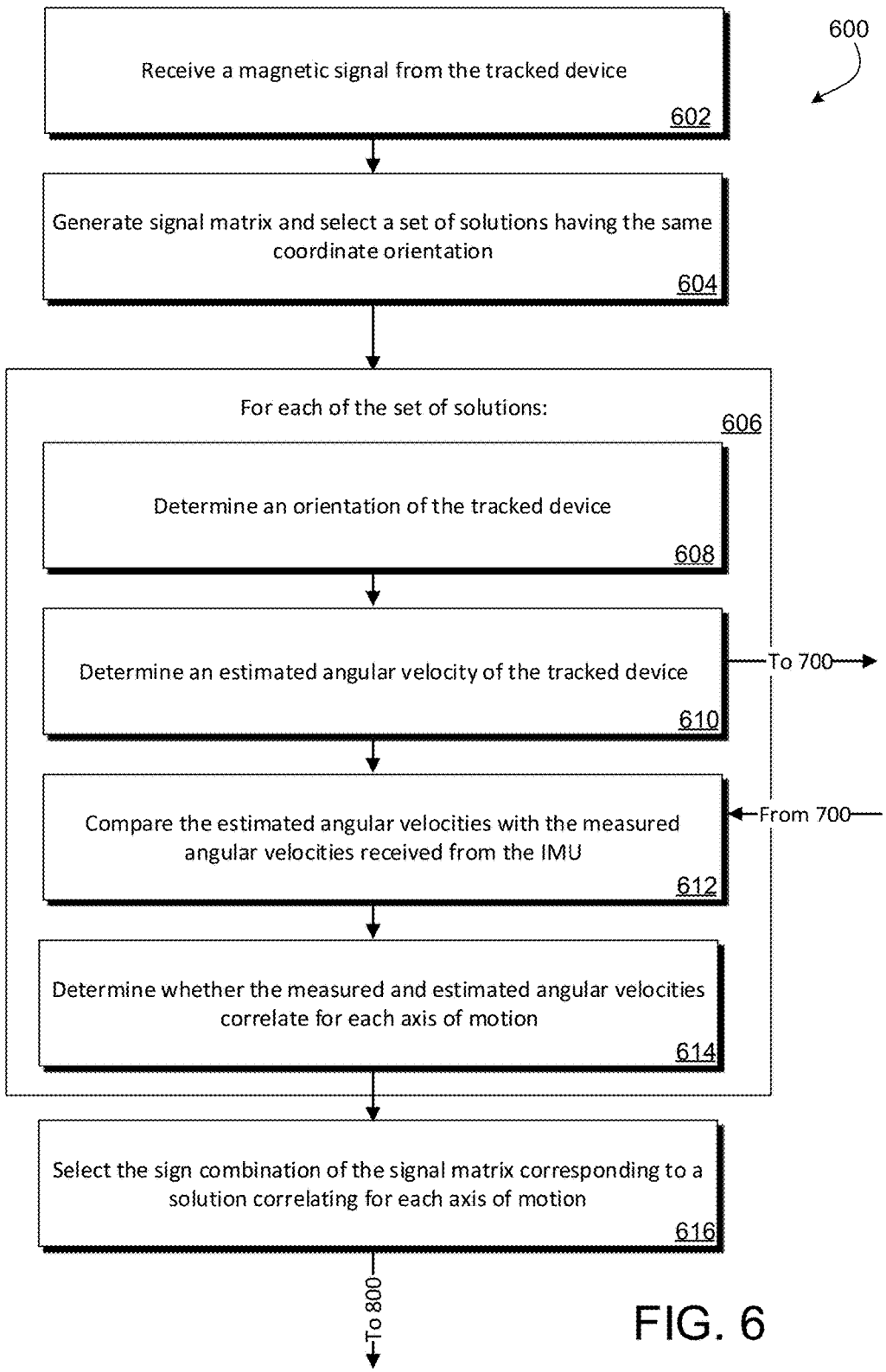

Turning to FIG. 6, a process 600 for performing PLL disambiguation is shown in a flow diagram. The process 600 can be performed by a computing system such as computing system 110 of the EMT system 100 of FIGS. 1A-1C. As described above. for PLL disambiguation includes testing each sign combinations associated with a possible pose solution of a tracked object (e.g., tracked device 102 of FIGS. 1A-1B). The computing device 110 can reduce processing time by discarding coordinate pairs that are associated with one of two coordinate orientations (e.g., left-handed solutions and right-handed solutions). The orientation of the tracked device 102 can be computed from the remaining solutions (e.g., right-handed solutions). In some implementations, a buffer of orientation data can be used by the computing device 110 to estimate angular velocity for each right-handed sign combination (or left-handed sign combination) and test for a match with the angular velocity reported by the gyroscope in the IMU 112. As described above, only the angular velocity from the correct sign combination should match the angular velocity reported by the gyroscope within a predetermined threshold, especially over consecutive frames of data.

To perform PLL disambiguation using inertial data from the IMU 112, the following steps are performed by the computing device 110. Similar to process 500, process 600 can be performed by a processing device in the computing device 110, and/or by one or more processors of the tracking device 104 (which may be a part of computing device 110).

The computing device 110 is configured to receive (602) a magnetic signal representing position and orientation data from the tracked device 102. The magnetic signal is decomposed into a signal matrix as described above in reference to FIG. 2.

The computing device 110 is configured to generate the signal matrix and select (602) a set of solutions (e.g., position and orientation coordinates) having the same coordinate orientation (e.g., either the set of right-handed solutions or the set of left-handed solutions). Generally, there are four solutions having the same coordinate orientation. To do this, the computing device 110 tests each possible sign combination to the signal matrix and compute the determinant for each sign combination. When the computing device 110 determines that the determinant is negative for a particular solution, the computing device 110 is configured to discard that sign combination as a potential solution. When each combination has been tested by the computing device 110, only four sign combinations are associated with a positive determinant and are kept for further analysis.

The computing device 110 is configured to test (606) each remaining solution, e.g., in sequence, in parallel, etc. For example, each remaining solution can be associated with a signal matrix having a sign combination resulting in a positive determinant sign. The computing device 110 is configured to determine (608) the orientation of the tracked device 102. In some implementations, the orientation is with respect to the IMU 112. Specifically, the orientation is of the environment in the frame of the IMU 112. The orientation coordinates are stored for use in the next frame (e.g., when the next magnetic signal is received) to compute angular velocity (e.g., using numerical differentiation).

The computing device 110 is configured to determine (610) an estimated (expected) angular velocity of the tracked device 102. In some implementations, the estimated angular velocity is a portion of the estimated inertial data. As described above, the estimated angular velocity of the tracked device 102 is determined based on a previous computed orientation of the tracked device (e.g., from the magnetic signal of a previous frame) and the current determined orientation of the tracked device 102. In some implementations, when right-handed solutions are used, for each of the four right-handed quaternions, process 700 described with respect to FIG. 7 is performed by the computing device 110 to determine the estimated angular velocity for each solution. In some implementations, the computing device 110 verifies that the estimated values do not exceed physical limits of the IMU 112. Such values can indicate that the solution is not correct, such as because of an error in computation or in the data, that the possible solution is invalid (e.g., physically impossible), that the result will be incorrect because of sensor limitations, etc. In some implementations, the computing device 110 is configured to store the estimated angular velocities (e.g., in a buffer).

The computing device 110 is configured to compare (612) the estimated angular velocities for each solution with the measured angular velocities received from the IMU 112. The computing device 110, for each of the four right-handed angular velocities, computes the cumulative sum between the respective estimated angular velocity and the measured angular velocity from the gyroscope. After sufficient frames have been collected, only one of the four cumulative sums should yield positive values for all x, y, and z axes. The computing device 110 is configured to determine (614) that the cumulative sum is positive for each axis of motion for a solution of the four possible solutions. The computing device 110 is configured to select (616) the solution with a sign combination corresponding to the positive cumulative sum for each axis of motion. The selected solution can be used by the computing device 110 as an input for hemisphere disambiguation, as there are two possible position solutions (one for each of the two hemisphere options).

Figure 7:
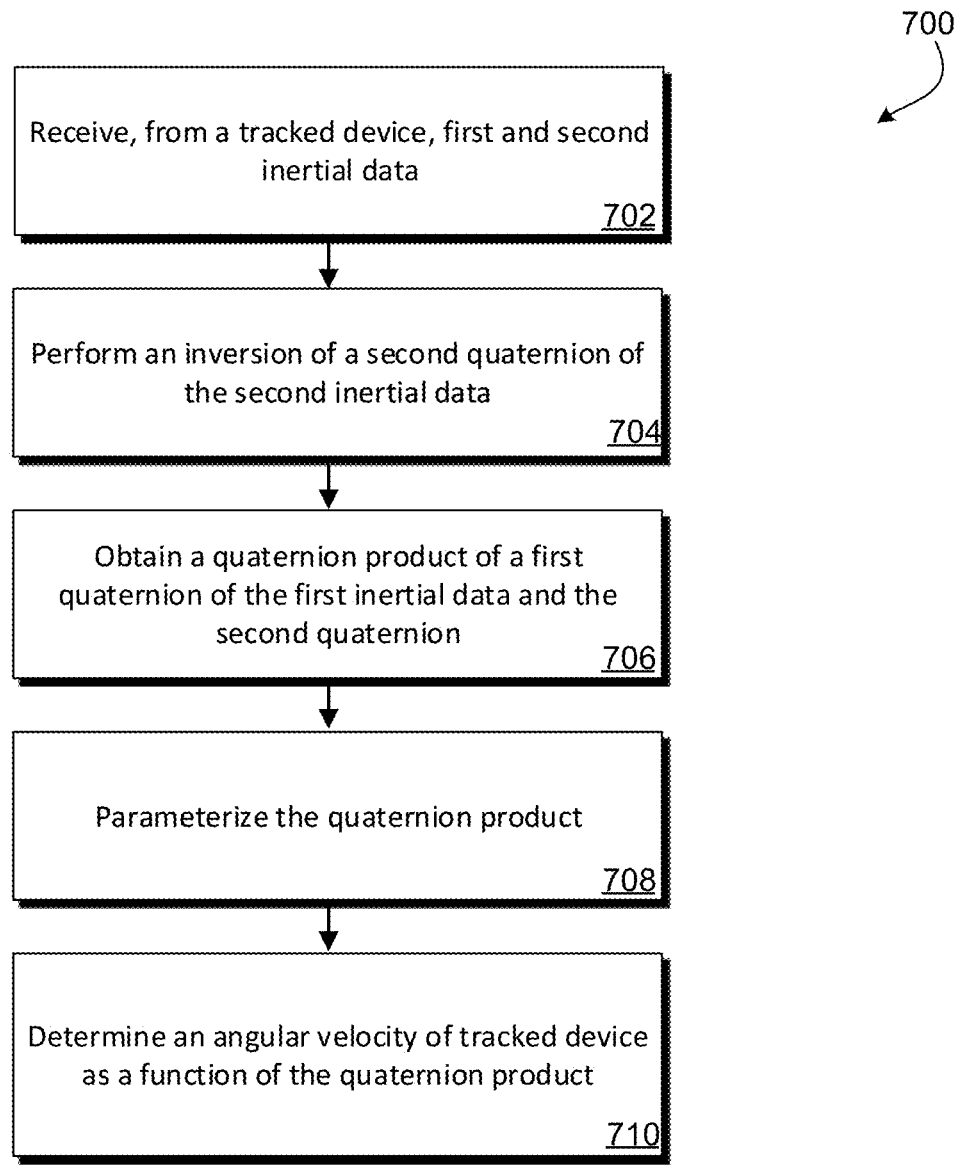

FIG. 7 shows an example flow diagram of a process 700 for determining the estimated angular velocity for each possible solution (e.g., the four solutions of process 600). The process 700 can be performed by a computing system such as computing system 110 of the EMT system 100 of FIGS. 1A-1C.

The computing device 110 is configured to receive (702), from a tracked device (e.g., tracked device 102 of FIG. 1A-1B), a first inertial data and second inertial data. In some implementations, the computing device 110 generates a first quaternion from the first inertial data. In some implementations, the first inertial data is measured at a first time. In some implementations, computing device 110 generates a second quaternion from the second inertial data. The second inertial data can be measured at a second time later than the first time.

The computing device 110 is configured to perform a quaternion inversion (704) the second quaternion. The computing device 110 is configured to obtain (706) a quaternion product of the first quaternion and the inverted second quaternion. The computing device 110 is configured to parameterize (708) the quaternion product. For example, the computing device 110 can use an axis-angle representation including an axis value and an angle value for the orientation quaternions. The computing device 110 is configured to determine (710) an angular velocity of the tracked device 102 as a function of the quaternion product. For example, the computing device 110 can divide a product of the axis value and the angle value by a time value representing a difference between the first time and the second time. Table 1 shows an example process for determining the estimated angular velocity of the tracked device.

TABLE 1

Example process for determining an estimated angular velocity of the tracked device.

$q_{diff} \leftarrow q_t - 1 \otimes q_t^{-1}$
$a, \theta \leftarrow \text{axis\_angle}(q_{diff})$
$\omega \leftarrow a * \theta/\Delta t$ In some implementations, for the process 700 to properly handle corner cases, the function axis_angle( ) is used by the computing device 110 to normalize the axis and return a zero vector in the case that $q_{diff}$ is the identity.

The computing device 110 estimates linear acceleration in the frame of the IMU to allow for a direct comparison between the measured linear acceleration and the estimated (expected) linear acceleration. Before computing linear acceleration, the pose (total motion value) of the IMU 112 should be inverted such that the motion's frame of reference becomes the IMU. The computing device 110 can then apply numerical differentiation (e.g., using the three point method) to the position component twice to estimate the linear acceleration. The estimated linear acceleration is missing the gravity contribution, which can be determined and either added into the estimation or removed from the measured linear acceleration.

Once the PLL disambiguation has been performed, the computing device 110 can determine the position of the tracked device 102 by disambiguating the hemisphere solutions. FIG. 8 shows an example flow diagram of a process 800 for tracking an object in an electromagnetic field by disambiguating the hemisphere solutions. The process 800 can be performed by a computing system such as computing system 110 of the EMT system 100 of FIGS. 1A-1C.

In some implementations, hemisphere disambiguation is similar to PLL disambiguation. Once the PLL signs have been (e.g., as described above with respect to processes 500, 600, and 700) the computing device 110 can determine a position and collect a buffer of linear acceleration values for each of the two hemisphere options. Only the computed linear acceleration from the correct hemisphere should match the acceleration reported by the IMU 112.

The computing device 110 is configured to receive (802), for the tracked device 102, position and orientation data of a magnetic signal. In some implementations, the position and orientation data include the signal matrix (e.g., of process 600) that has a sign combination solution selected. The signal matrix thus has two hemisphere options. From the signal matrix available, and for each of the two hemisphere options, the computing device 110 determines (806) the total motion of the IMU 112 in the frame of the environment. The computing device 110 determines the motion of the tracked device 102 in a world frame by comparing a first motion measurement from the IMU 112 with respect to a second motion measurement of the IMU. In some implementations, the computing device 110 is configured to invert (808) the IMU 112 inertial data so that the inertial data is represented in the frame of the IMU.

The computing device 110 is configured to estimate a linear acceleration for each of the two hemisphere options. The computing device 110 is configured to determine (810) an estimated linear acceleration value for the tracked device based on hemisphere options of a prior position and orientation measurement. For example, for each hemisphere option, the linear acceleration is estimated based on a prior measurement of the magnetic signal for that hemisphere option.

The computing device 110 is configured to adjust (812) a linear acceleration value based on a gravity value estimate. In some implementations, the gravity estimate is added to the estimated linear accelerations. In some implementations, the gravity estimate is removed from the measured linear acceleration received from the tracked device 102.

The computing device 110 is configured to determine (814) a cumulative sum for each of the two hemisphere options. In some implementations, a cumulative sum of the measured and estimated values and the measured values of the linear accelerations in each of the x, y, and z axes can be generated. A positive correlation is found when the sum exceeds a threshold value for all three axes. For each incorrect solution, fewer than all three axes will be associated with a positive cumulative sum. For example, zero, one, or two of the axes may yield a positive cumulative sum over a threshold number of frames of measured magnetic signals. The hemisphere solution with positive correlations for each of the three axes is selected (816) by the computing device 110. The computing device 110 can output the selected solution for use in any number of applications, as described above.

The EMT system 100 described above can be implemented using software included on a computer-readable medium for execution on a computer (e.g., the computing device 110 of FIG. 1A). For example, the software may form procedures in one or more computer programs that execute on one or more programmed or programmable computer systems (which may be of various architectures).

Figure 9:
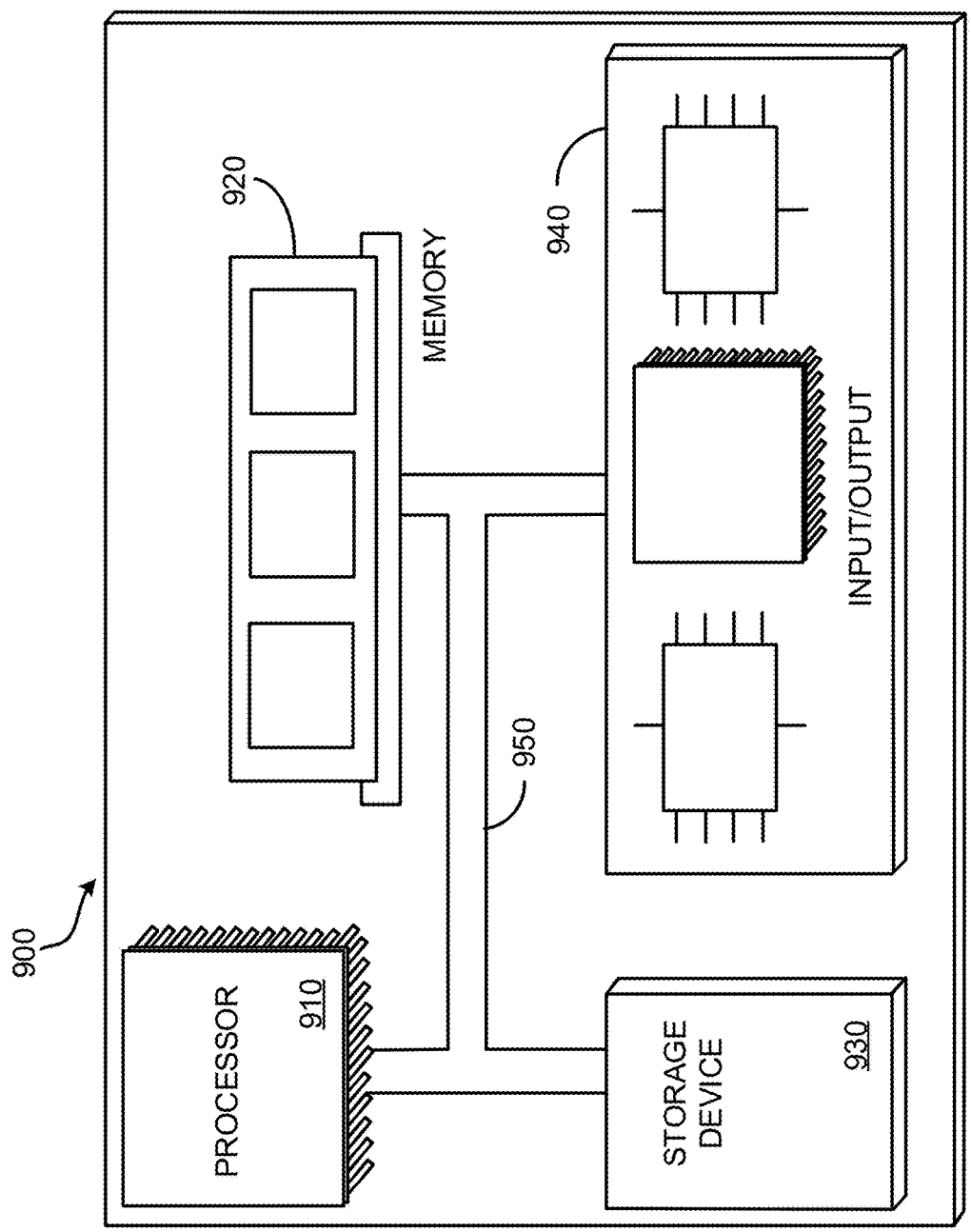
FIG. 9 is a block diagram of an example computer system.

FIG. 9 is a block diagram of an example computer system 900. The computing device 110 of FIG. 1A may be an example of the computer system 900 described here. The system 900 can include a processor 910, a memory 920, a storage device 930, and an input/output device 940. Each of the components 910, 920, 930, and 940 can be interconnected, for example, using a system bus 950. The processor 910 is capable of processing instructions for execution within the system 900. The processor 910 can be a single-threaded processor, a multi-threaded processor, or a quantum computer. The processor 910 is capable of processing instructions stored in the memory 920 or on the storage device 930. The processor 910 may execute operations such as causing the EMT system 100 to determine the position and/or the orientation of tracked device 102.

The memory 920 stores information within the system 900. In some implementations, the memory 920 is a computer-readable medium. The memory 920 can, for example, be a volatile memory unit or a non-volatile memory unit.

The storage device 930 is capable of providing mass storage for the system 900. In some implementations, the storage device 930 is a non-transitory computer-readable medium. The storage device 930 can include, for example, a hard disk device, an optical disk device, a solid-date drive, a flash drive, magnetic tape, or some other large capacity storage device. The storage device 930 may alternatively be a cloud storage device, e.g., a logical storage device including multiple physical storage devices distributed on a network and accessed using a network. In some implementations, the information stored on the memory 920 can also or instead be stored on the storage device 930.

The input/output device 940 provides input/output operations for the system 900. In some implementations, the input/output device 940 includes one or more of network interface devices (e.g., an Ethernet card), a serial communication device (e.g., an RS-232 10 port), and/or a wireless interface device (e.g., a short-range wireless communication device, an 902.11 card, a 3G wireless modem, or a 4G wireless modem). In some implementations, the input/output device 940 includes driver devices configured to receive input data and send output data to other input/output devices, e.g., a keyboard, a printer, and display devices. In some implementations, mobile computing devices, mobile communication devices, and other devices are used.

In some implementations, the system 900 is a microcontroller. A microcontroller is a device that contains multiple elements of a computer system in a single electronics package. For example, the single electronics package could contain the processor 910, the memory 920, the storage device 930, and input/output devices 940.

Although an example computer system has been described in FIG. 9, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of nonvolatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments have been described. Nevertheless, it will be understood that various modifications may be made without departing from the spirit and scope of the subject matter described herein. Other such embodiments are within the scope of the following claims.

What is claimed is:

1. A system comprising:
   a tracked device comprising:
      an inertial measurement unit (IMU) configured to generate inertial data; and
      an emitter configured to generate an electromagnetic signal;
   a tracking device comprising:
      a magnetic sensor configured to receive the electromagnetic signal from the tracked device; and
      a receiver configured to receive the inertial data from the tracked device; and
   a computing device comprising one or more processors, the computing device configured to perform operations comprising:
      determining a set of possible positions and orientations of the tracked device relative to the tracking device based on the electromagnetic signal;
      receiving a measured inertial value of the inertial data representing a motion of the tracked device;
      determining an estimated inertial value corresponding to the motion of the tracked device based on at least one position and orientation of the set of possible positions and orientations;
      determining a difference value representing a difference between the estimated inertial value and the measured inertial value;
      in response to determining the difference value, determining a particular position and a particular orientation from the set of possible positions and orientations; and
      generating an output comprising the particular position and the particular orientation.

2. The system of claim 1, wherein, for each frame in a series of frames, the difference value is determined for that frame, and wherein the difference values are summed and compared to a threshold value.

3. The system of claim 1, wherein the measured inertial value comprises a linear acceleration value.

4. The system of claim 1, wherein the measured inertial value comprises an angular velocity value.

5. The system of claim 1, wherein the tracked device comprises one or more input devices, the one or more input devices configured to generate input signals comprising instructions for the computing device, and wherein the tracked device is configured to transmit the input signals to the computing device.

6. The system of claim 1, the electromagnetic signal corresponds to a first timestamp, and another electromagnetic signal received by the tracking device corresponds to a second timestamp representing a later time than the first timestamp.

7. The system of claim 1, further comprising a base station configured to provide a second electromagnetic signal from a second emitter, the base station is configured to provide reference frame for the tracked device and the tracking device, and wherein the particular position and the particular orientation are represented in coordinates of the reference frame.

8. The system of claim 1, wherein determining the estimated inertial value comprises generating a set of estimated inertial values, each estimated inertial value being based a pair of corresponding positions and orientations of the set of possible positions and orientations and another set of possible positions and orientations corresponding to a different measurement of the electromagnetic signal.

9. The system of claim 1, wherein the difference value comprises a set of values, each value of the set corresponding to an axis of motion of the tracked device, and wherein the particular position and the particular orientation correspond to a set of values that are each positive.

10. The system of claim 1, wherein the operations further comprise determining a gravitational component for the measured inertial value and correcting the measured inertial value based on the gravitational component.

11. The system of claim 1, wherein the electromagnetic signal is represented as a 3×3 matrix of data.

12. The system of claim 1, wherein the tracked device, the tracking device, and the computing device are a portion of one or more of a Virtual Reality (VR) system, an Augmented Reality (AR) system, a Mixed Reality (MR) system, and an extended reality (XR) system.

13. The system of claim 1, wherein the tracking device is configured to couple to a head-mounted display (HMD).

14. The system of claim 1, wherein the IMU comprises at least one accelerometer and at least one gyroscope.

15. The system of claim 1, wherein the computing device is configured to perform the operations during an initialization phase of operation of the system.

16. The system of claim 1, wherein the tracked device comprises a medical instrument.

17. The system of claim 1, wherein the tracked device is represented in a graphical user interface at the particular position and the particular orientation relative to the tracking device.

18. The system of claim 1, wherein the electromagnetic signal is modulated at a particular frequency that is associated with the tracked device, the particular frequency allowing the tracking device to identify the tracked device as the source of the electromagnetic signal.

19. The system of claim 1, wherein the output comprises a timestamp associated with the particular position and the particular orientation.

20. The system of claim 1, wherein the output comprises an identifier that identifies the tracked device as being associated with the particular position and the particular orientation.

21. A computer-implemented method comprising:
receiving, at a tracking device, an electromagnetic signal generated by a tracked device;
determining, based on the electromagnetic signal, a set of possible positions and orientations of the tracked device relative to the tracking device;
receiving, at the tracking device, a measured inertial value representing a motion of the tracked device;
determining an estimated inertial value corresponding to the motion of the tracked device based on at least one position and orientation of the set of possible positions and orientations;
determining a difference value representing a difference between the estimated inertial value and the measured inertial value;
in response to determining the difference value, determining a particular position and a particular orientation from the set of possible positions and orientations; and
generating an output comprising the particular position and the particular orientation.

22. A non-transitory computer readable medium storing instructions that are executable by one or more processors configured to perform operations comprising:
receiving, at a tracking device, an electromagnetic signal generated by a tracked device;
determining, based on the electromagnetic signal, a set of possible positions and orientations of the tracked device relative to the tracking device;
receiving, at the tracking device, a measured inertial value representing a motion of the tracked device;
determining an estimated inertial value corresponding to the motion of the tracked device based on at least one position and orientation of the set of possible positions and orientations;
determining a difference value representing a difference between the estimated inertial value and the measured inertial value;
in response to determining the difference value, determining a particular position and a particular orientation from the set of possible positions and orientations; and
generating an output comprising the particular position and the particular orientation.

\* \* \* \* \*